United States Patent [19]

Fuchs et al.

[11] 4,360,690
[45] Nov. 23, 1982

[54] COMBATING PESTS WITH 1-ARYL-CYCLOPROPANE-1-CARBOXYLIC ACID ESTERS

[75] Inventors: Rainer Fuchs, Wuppertal; Klaus Naumann, Leverkusen; Ingeborg Hammann, Cologne; Bernhard Homeyer, Leverkusen; Wolfgang Behrenz, Overath; Wilhelm Stendel, Wuppertal, all of Fed. Rep. of Germany

[73] Assignee: Bayer Aktiengesellschaft, Leverkusen, Fed. Rep. of Germany

[21] Appl. No.: 272,863

[22] Filed: Jun. 12, 1981

[30] Foreign Application Priority Data

Jul. 3, 1980 [DE] Fed. Rep. of Germany ....... 3025218

[51] Int. Cl.$^3$ ............................................. C07C 69/76
[52] U.S. Cl. ...................................... 560/57; 560/18; 560/21; 560/47; 560/48; 560/102; 260/465 D; 424/308; 424/309; 549/362; 549/366; 549/442; 549/443; 549/447
[58] Field of Search .................... 560/102, 57, 18, 21, 560/47, 48, 57, 102; 424/308, 309; 260/340.3, 340.5 R, 465 D

[56] References Cited

U.S. PATENT DOCUMENTS 4,220,591 9/1980 Holan et al. ........................ 560/102

*Primary Examiner*—Paul J. Killos
*Attorney, Agent, or Firm*—Sprung, Horn, Kramer & Woods

[57] ABSTRACT

1-Aryl-cyclopropane-1-carboxylic acid esters of the formula

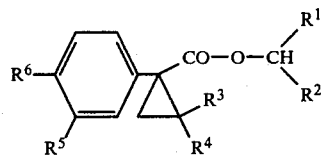

in which
  $R^1$ represents a hydrogen atom, a cyano radical or an alkyl, alkenyl or alkinyl radical within each case up to 7 carbon atoms, and
  $R^2$ represents a phenyl radical which is substituted by halogen and/or optionally halogen-substituted phenoxy, with the proviso that the radical $R^2$ in total contains at least one fluorine substituent,
  $R^3$ and $R^4$, which can be identical or different, represents a fluorine, chlorine or bromine atom or a methyl radical,
  $R^5$ represents a hydrogen or halogen atom or a methyl or methoxy radical, and
  $R^6$ represents a hydrogen or halogen atom, a cyano nitro or amino radical or an optionally halogen-substituted radical selected from $C_1$ to $C_4$ alkyl, $C_1$ to $C_4$ alkoxy and $C_1$ to $C_4$ alkylthio,
or wherein
  the two radicals $R^5$ and $R^6$ together represent an optionally halogen-substituted $C_1$ or $C_2$ alkylenedioxy radical,
which possess pesticidal properties.

10 Claims, No Drawings

COMBATING PESTS WITH 1-ARYL-CYCLOPROPANE-1-CARBOXYLIC ACID ESTERS

The invention relates to certain new 1-aryl-cyclopropane-1-carboxylic acid esters, to a process for their production and to their use as agents for combating pests, especially as insecticides and acaricides.

It is known that certain cyclopropanecarboxylic acid esters, such as 3-(2-methyl-1-propenyl)-2,2-dimethylcyclopropane-1-carboxylic acid 3-phenoxy-benzyl ester (phenothrin), have an insecticidal action (see British Patent Specification No. 1,243,858).

However, the action of these compounds is not always satisfactory, especially in the case of low concentrations of active compound and when small amounts are applied.

The present invention now provides, as new compounds, the 1-aryl-cyclopropane-1-carboxylic acid esters of the general formula

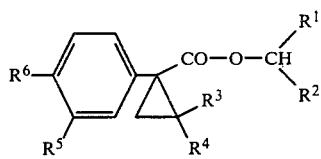  (I)

in which
R$^1$ represents a hydrogen atom, a cyano radical or an alkyl, alkenyl or alkinyl radical with in each case up to 4 carbon atoms, and
R$^2$ represents a phenyl radical which is substituted by halogen and/or optionally halogen-substituted phenoxy, with the proviso that the radical R$^2$ in total contains at least one fluorine substituent,
R$^3$ and R$^4$, which can be identical or different, represent a fluorine, chlorine or bromine atom or a methyl radical,
R$^5$ represents a hydrogen or halogen atom or a methyl or methoxy radical and
R$^6$ represents a hydrogen or halogen atom, a cyano, nitro or amino radical or an optionally halogen-substituted radical selected from C$_1$ to C$_4$ alkyl, C$_1$ to C$_4$ alkoxy and C$_1$ to C$_4$ alkylthio,
or wherein
the two radicals R$^5$ and R$^6$ together represent an optionally halogen-substituted C$_1$ or C$_2$ alkylenedioxy radical.

The compounds of general formula (I) can exist in the various possible stereoisomer and optically active isomer forms, as well as mixtures thereof.

According to the present invention there is further provided a process for the production of a compound of the present invention, characterized in that a 1-aryl-cycloproapne-1-carboxylic acid of the general formula

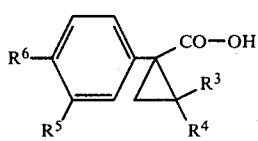  (II)

in which R$^3$, R$^4$, R$^5$ and R$^6$ have the abovementioned meanings, or a reactive derivative thereof, is reacted with a benzyl alcohol of the general formula

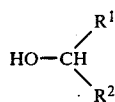  (III)

in which R$^1$ and R$^2$ have the abovementioned meanings, or with a reactive derivative thereof, if appropriate in the presence of an acid acceptor and/or a catalyst and if appropriate using a diluent.

The 1-aryl-cyclopropane-1-carboxylic acid esters of the formula (I) are distinguished by a high pesticidal activity.

Surprisingly, the compounds of the present invention exhibit a considerably more powerful insecticidal and acaricidal action than the compounds of analogous structure and the same type of action which are known from the state of the art.

Preferred compounds of the present invention are those in which,
R$^1$ represents a hydrogen atom or a cyano radical,
R$^2$ represents a 4-fluoro-3-phenoxy-phenyl, 3-(4-fluoro-phenoxy)-phenyl, 4-fluoro-3-(4-fluorophenoxy)-phenyl or pentafluorophenyl radical,
R$^3$ and R$^4$ represent chlorine atoms,
R$^5$ represents a hydrogen atom and
R$^6$ represents a fluorine, chlorine or bromine atom or a methoxy, ethoxy, trifluoromethoxy, 2-chloro-1,1,2-trifluoroethoxy or 1,1,2,2-tetrafluoroethoxy radical,
or wherein
R$^5$ and R$^6$ together represent a methylenedioxy or difluoromethylenedioxy radical.

In a preferred process variant (a) of the preparative process for a compound of the formula (I), a 1-aryl-cyclopropane-1-carboxylic acid chloride of the general formula

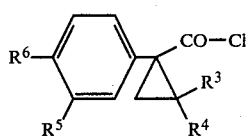  (II a)

in which R$^3$, R$^4$, R$^5$ and R$^6$ have the abovementioned meanings, is reacted with a benzyl alcohol of the formula (III) above, in the presence of an acid acceptor, and using a diluent.

In another preferred process variant (b), for the preparation of a compound of the formula (I) in which R$^1$ represents cyano and R$^2$ represents fluorine-substituted phenoxy-phenyl, the acid chloride of the formula (II a), above, is reacted with an appropriate phenoxy-benzaldehyde of the general formula

 OCH—R$^2$  (IV)

in which R$^2$ represents fluorine-substituted phenoxyphenyl, and at least the equimolar amount of an alkali metal cyanide (especially sodium cyanide or potassium cyanide) in the presence of water and a water-immiscible organic solvent, and if appropriate in the presence of a catalyst.

Other reactive derivatives of the carboxylic acids of the formula (II) which may be mentioned are $C_1$ to $C_4$ alkyl esters thereof, which can be reacted with alcohols of the formula (III) by customary methods.

Alkali metal salts, alkaline earth metal salts or ammonium salts of the carboxylic acids of formula (II) can also be reacted with benzyl halides, which are derived from the benzyl alcohols of the formula (III), to give compounds of the formula (I).

If, for example, 1-(4-trifluoromethoxy-phenyl)-2,2-dichloro-cyclopropane-1-carboxylic acid chloride and pentafluorobenzyl alcohol are used as starting substances in process variant (a), and 1-(4-(2-chloro-1,1,2-trifluoroethoxy-phenyl)-2,2-dichloro-cyclopropane-1-carboxylic acid chloride, 3-(4-fluoro-phenoxy)-benzaldehyde and sodium cyanide are used as starting substances in variant (b), the reactions which proceed in the two process variants can be outlined by the following equations:

phenyl)-2,2-dichloro-cyclopropane-1-carboxylic acid and the corresponding acid chlorides.

1-Aryl-cyclopropane-1-carboxylic acids of the formula (II) are known (see DE-OS (German Published Specification) No. 2,653,189).

The corresponding acid chlorides of the formula (II a) are obtained therefrom in the customary manner, for example by reaction with thionyl chloride, if appropriate in the presence of a diluent (such as carbon tetrachloride) at a temperature between 10° and 100° C.

Preferred benzyl alcohols of formula (III) to be used as starting substances are those in which $R^1$ and $R^2$ represent those radicals which have already been mentioned in the definition of the preferred compounds of the present invention.

Examples of the starting compounds of the formula (III) which may be mentioned are: pentafluorobenzyl alcohol, 4-fluoro-3-phenoxy-benzyl alcohol, 3-(4-fluorophenoxy)-benzyl alcohol, 4-fluoro-3-(4-fluorophenoxy)-benzyl alcohol and 3-(4-fluoro-phenoxy)-α-cyano-benzyl alcohol.

The starting compounds of the formula (III) are already known (see British Patent Specification No. 1,078,511 and DE-OS'en (German Published Specifica-

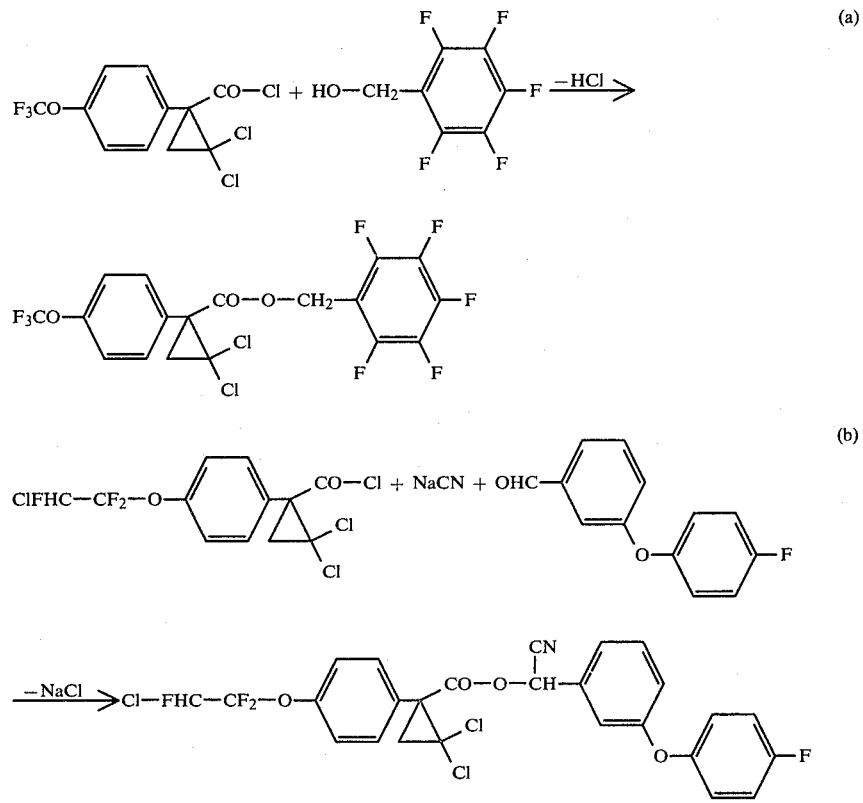

Preferred 1-aryl-cyclopropane-1-carboxylic acids of formula (II) to be used as starting substances are those in which $R^3$, $R^4$, $R^5$ and $R^6$ represent those radicals which have already been mentioned as in the definition of preferred compounds of the present invention.

Examples of the starting compounds of the formula (II) and of the corresponding acid chlorides of the formula (II a) which may be mentioned are: 1-(4-fluoro-phenyl)-, 1-(4-chloro-phenyl)-, 1-(4-bromo-phenyl)-, 1-(4-methoxy-phenyl)-, 1-(4-ethoxy-phenyl)-, 1-(3,4-methylenedioxy-phenyl)- and 1-(4-trifluoromethoxytion) Nos. 2,621,433, 2,709,264 and U.S. application Ser. No. 932,597, filed Aug. 10, 1978.

Preferred phenoxy-benzaldehydes of formula (IV) which can be used as starting substances are those in which $R^2$ represents those radicals which have already been mentioned in the definition of $R^2$ in the preferred compounds of the present invention. Examples which may be mentioned are: 4-fluoro-3-phenoxy-benzaldehyde, 3-(4-fluoro-phenoxy)-benzaldehyde and 4-fluoro-3-(4-fluoro-phenoxy)-benzaldehyde.

The phenoxybenzaldehydes of the formula (IV) are already known from the specifications noted hereinabove.

All variants of the process for the preparation of the compounds of the formula (I) are preferably carried out using a diluent. Possible diluents are virtually any of the inert organic solvents. These include, as preferences, aliphatic and aromatic, optionally halogenated hydrocarbons (such as pentane, hexane, heptane, cyclohexane, petroleum ether, benzine, ligroin, benzene, toluene, xylene, methylene chloride, ethylene chloride, chloroform, carbon tetrachloride, chlorobenzene and o-dichlorobenzene), ethers (such as diethyl ether, dibutyl ether, glycol dimethyl ether and diglycol dimethyl ether, tetrahydrofuran and dioxane), ketones, (such as acetone, methyl ethyl ketone, methyl isopropyl ketone and methyl isobutyl ketone), esters (such as methyl acetate and ethyl acetate), nitriles (such as acetonitrile and propionitrile), amides (such as dimethylformamide, dimethylacetamide and N-methylpyrrolidone), dimethylsulphoxide, tetramethylene sulphone and hexamethylphosphoric acid triamide.

Variant (a) of the process according to the invention is preferably carried out in the presence of an acid acceptor. Any customary acid-binding agent can be used as the acid acceptor. Acid-binding agents which have proved particularly suitable are alkali metal carbonates and alcoholates (such as sodium carbonate, potassium carbonate, sodium methylate or ethylate or potassium methylate or ethylate), and aliphatic, aromatic or heterocyclic amines (for example triethylamine, trimethylamine, dimethylaniline, dimethylbenzylamine, pyridine, diazabicyclooctane, diazabicyclononene and diazabicycloundecene).

Variant (b) of the process according to the invention is generally carried out in the presence of water and one of the abovementioned organic solvents, as long as this is water-immiscible. The abovementioned hydrocarbons are particularly suitable here.

Compounds which are suitable for transferring anions from water into organic solvents are preferably used as the catalysts in process variant (b). Examples of these compounds are benzyl-triethyl-ammonium bisulphate, tetrabutylammonium bromide and methyl-trioctylammonium chloride (Aliquat 336).

The reaction temperature can be varied within a substantial range in all process variants. In general, the reaction is carried out at between 0° and 100° C., preferably at from 10° to 50° C.

The process according to the invention is in general carried out under normal pressure. The starting substances are usually employed in equimolar amounts for carrying out the process according to the invention. An excess of any of the reactants provides no substantial advantages. The starting substances are brought together in a suitable diluent and stirred, if appropriate after adding an acid acceptor and/or a catalyst, until the reaction has ended.

Working up can be carried out by customary methods, for example by a procedure in which, if appropriate, the reaction mixture is diluted with water and/or a water-immiscible organic solvent, such as, for example, toluene, the organic phase is separated off, washed with water, dried and filtered and the solvent is carefully distilled off from the filtrate under reduced pressure and at moderately elevated temperature ("incipient distillation").

The active compounds are well tolerated by plants, have a favorable level of toxicity to warm-blooded animals, and are suitable for combating anthropod pests, especially insects and Arachnida, which are encountered in agriculture, in forestry, in the protection of stored products and of materials, and in the hygiene field. They are active against normally sensitive and resistant species and against all or some stages of development. The abovementioned pests include:

From the class of the Isopoda, for example *Oniscus asellus, Armadillidium vulgare* and *Porcello scaber;* from the class of the Diplopoda, for example *Blaniulus guttulatus;* from the class of the Chilopoda, for example *Geophilus carpophagus* and *Scutigera* spec.;

from the class of the Symphyla, for example *Scutigerella immaculata;* from the order of the Thysanura, for example *Lepisma saccharina;* from the order of the Collembola, for example *Onychiurus armatus;* from the order of the Orthoptera, for example *Blatta orientalis, Periplaneta americana, Leucophaea maderae, Blattella germanica, Acheta domesticus, Gryllotalpa* spp., *Locusta migratoria migratorioides, Melanoplus differentialis* and *Schistocerca gregaria;* from the order of the Dermaptera, for example *Forficula auricularia;* from the order of the Isoptera, for example *Reticulitermes* spp.;

from the order of the Anoplura, for example *Phylloxera vastatrix, Pemphigus* spp., *Pediculus humanus corporis, Haematopinus* spp. and *Linognathus* spp.;

from the order of the Mallophaga, for example *Trichodectes* spp. and *Damalinea* spp.;

from the order of the Thysanoptera, for example *Hercinothrips femoralis* and *Thrips tabaci;* from the order of the Heteroptera, for example *Eurygaster* spp., *Dysdercus intermedius, Piesma quadrata, Cimex lectularius, Rhodnius prolixus* and *Triatoma* spp.;

from the order of the Homoptera, for example *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae, Myzus* spp., *Phorodon humuli, Rhopalosiphum padi, Empoasca* spp., *Euscelis bilobatus, Nephotettix cincticeps, Lecanium corni, Saissetia oleae, Laodelphax striatellus, Nilaparvata lugens, Aonidiella aurantii, Aspidiotus hederae, Pseudococcus* spp. and *Psylla* spp.;

from the order of the Lepidoptera, for example *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea, Lymantria* spp., *Bucculatrix thurberiella, Phyllocnistis citrella, Agrotis* spp., *Euxoa* spp., *Feltia* spp., *Earias insulana, Heliothis* spp., *Laphygma exigua, Mamestra brassicae, Panolis flammea, Prodenia litura, Spodoptera* spp., *Trichoplusia ni, Carpocapsa pomonella, Pieris* spp., *Chilo* spp., *Pyrausta nubilalis, Ephestia kuehniella, Galleria mellonella, Cacoecia podana, Capua reticulana, Choristoneura fumiferana, Clysia ambiguella, Homona magnanima* and *Tortrix viridana;* from the order of the Coleoptera, for example *Anobium punctatum, Rhizopertha dominica, Bruchidius obtectus, Acanthoscelides obtectus, Hylotrupes bajulus, Agelastica alni, Leptinotarsa decemlineata, Phaedon co-*

*chleariae, Diabrotica* spp., *Psylliodes chrysocephala, Epilachna varivestis, Atomaria* spp., *Oryzaephilus surinamensis, Anthonomus* spp., *Sitophilus* spp., *Otiorrhynchus sulcatus, Cosmopolites sordidus, Ceuthorrhynchus assimilis, Hypera postica, Dermestes* spp., *Trogoderma* spp., *Anthrenus* spp., *Attagenus* spp., *Lyctus* spp., *Meligethes aeneus, Ptinus* spp., *Niptus hololeucus, Gibbium psylloides, Tribolium* spp., *Tenebrio molitor, Agriotes* spp., *Conoderus* spp., *Melolontha melolontha, Amphimallon solstitialis* and *Costelytra zealandica;* from the order of the Hymenoptera, for example *Diprion* spp., *Hoplocampa* spp., *Lasius* spp., *Monomorium pharaonis* and *Vespa* spp.;

from the order of the Diptera, for example *Aedes* spp., *Anopheles* spp., *Culex* spp., *Drosophila melanogaster, Musca* spp., *Fannia* spp., *Calliphora erythrocephala, Lucilia* spp., *Chrysomyia* spp., *Cuterebra* spp., *Gastrophilus* spp., *Hyppobosca* spp., *Stomoxys* spp., *Oestrus* spp., *Hypoderma* spp., *Tabanus* spp., *Tannia* spp., *Bibio hortulanus, Oscinella frit, Phorbia* spp., *Pegomyia hyoscyami, Ceratitis capitata, Dacus oleae* and *Tipula paludosa;* from the order of the Siphonaptera, for example *Xenopsylla cheopis* and *Ceratophyllus* spp.;

from the class of the Arachnida, for example *Scorpio maurus* and *Latrodectus mactans;* from the order of the Acarina, for example *Acarus siro, Argas* spp., *Ornithodoros* spp., *Dermanyssus gallinae, Eriophyes ribis, Phyllocoptruta oleivora, Boophilus* spp., *Rhipicephalus* spp., *Amblyomma* spp., *Hyalomma* spp., *Ixodes* spp., *Psoroptes* spp., *Chorioptes* spp., *Sarcoptes* spp., *Tarsonemus* spp., *Bryobia praetiosa, Panonychus* spp. and *Tetranychus* spp.

The active compounds can be converted to the customary formulations, such as solutions, emulsions, suspensions, powders, foams, pastes, granules, aerosols, natural and synthetic materials impregnated with active compound, very fine capsules in polymeric substances and in coating compositions for seed, and formulations used with burning equipment, such as fumigating cartridges, fumigating cans, fumigating coils and the like, as well as ULV cold mist and warm mist formulations.

These formulations may be produced in known-manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

A solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95 percent by weight of active compound, preferably from 0.5 to 90 percent by weight.

The active compounds according to the invention may be used in the form of their formulations of the types that are commercially available or in the use forms prepared from these formulations.

The active compound content of the use forms prepared from the formulations of the types that are commercially available can vary within wide ranges. The active compound concentration of the use forms can be from 0.0000001 to 100% by weight of active compound, preferably from 0.0001 to 1% by weight.

The active compounds according to the invention can be present in their commercially available formulations and in the use forms, prepared from these formulations, as a mixture with other active compounds, such as insecticides, baits, sterilizing agents, acaricides, nematicides, fungicides, growth-regulating substances or herbicides. The insecticides include, for example, phosphates, carbamates, carboxylates, chlorinated hydrocarbons, phenylureas and substances produced by microorganisms.

The active compounds according to the invention can furthermore be present in their commercially available formulations and in the use forms, prepared from these formulations, as a mixture with synergistic agents. Synergistic agents are compounds which increase the action of the active compounds, without it being necessary for the synergistic agent added to be active itself.

When used against pests harmful to health and pests of stored products, the active compounds are distinguished by an excellent residual action on wood and clay as well as a good stability to alkali on limed substrates.

The active compounds according to the invention are also suitable for combating ectoparasites and endoparasites in the field of veterinary medicine.

The present invention also provides a pesticidal composition containing as active ingredient a compound of the present invention in admixture with a solid or liquefied gaseous diluent or carrier or in admixture with a liquid diluent or carrier containing a surface-active agent.

The present invention also provides a method of combating pests (in particular arthropods, especially insects or acarids) which comprises applying to the pests, or to a habitat thereof, a compound of the present invention alone or in the form of a composition containing as active ingredient a compound of the present invention in admixture with a diluent or carrier.

The present invention also provides a method of freeing or protecting domesticated animals from parasites which comprises applying to said animals a compound according to the present invention, in admixture with a diluent or carrier.

The present invention further provides crops protected from damage by pest by being grown in areas in which immediately prior to and/or during the time of the growing a compound of the present invention was applied alone or in admixture with a diluent or carrier.

It will be seen that the usual methods of providing a harvested crop may be improved by the present invention.

The present invention further provides domesticated animals whenever freed or protected from parasites by the application to said animals of a compound according to the present invention, in admixture with a diluent or carrier.

The active compounds according to the invention may be used in a known manner in the veterinary sector, such as by oral administration, for example in the form of tablets, capsules, drinks and granules, by dermal application, for example by means of dipping, spraying, pouring on, spotting on, and dusting, and by parenteral administration, for example by means of an injection.

PREPARATIVE EXAMPLES

Example 1

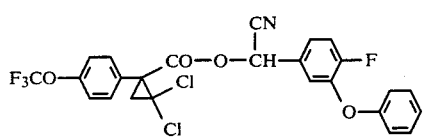

(1)

5.67 g (0.017 mole) of (±)-1-(4-trifluoromethoxy-phenyl)-2,2-dichlorocyclopropane-1-carboxylic acid chloride and 3.67 g (0.017 mole) of 3-phenoxy-4-fluoro-benzaldehyde were together added dropwise to a mixture of 1.13 g of sodium cyanide, 1.7 ml of water, 100 ml of n-hexane and 0.6 g of tetrabutylammonium bromide at 20°–25° C., while stirring, and the mixture was then stirred at 20° to 25° C. for 4 hours. 300 ml of toluene were then added to the reaction mixture and the mixture was extracted twice by shaking with 300 ml of water each time. The organic phase was separated off and dried over magnesium sulphate and the solvent was distilled off under a waterpump vacuum. Last residues of solvent were removed by brief incipient distillation at a bath temperature of 60° C./1 mm Hg. 7 g (76.3% of theory) of (±)-1-(4-trifluoromethoxy-phenyl)-2,2-dichlorocyclopropane-1-carboxylic acid 3-phenoxy-4-fluoro-(±)-α-cyano-benzyl ester were obtained as a yellow oil. The structure was confirmed by the $^1$H-NMR spectrum.

$^1$H-NMR spectrum of CDCl$_3$/τ(ppm):
Benzyl H: 3.74 (d/1H)
Cyclopropane H: 7.60 (quartet/2H)

The following compound was obtained analogously:

EXAMPLE 2

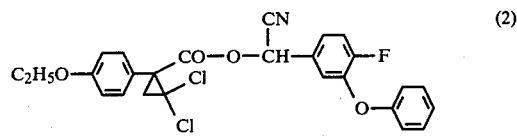

(2)

$^1$H-NMR spectrum in CDCl$_3$/τ(ppm):
Benzyl H: 6.15 (1H)
Cyclopropane H: 2.25 (quartet/2H)

EXAMPLE 3

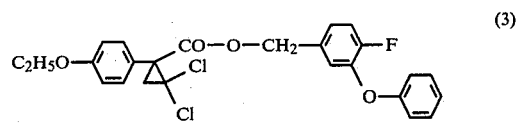

(3)

5.87 g (0.02 mole) of (±)-1-(4-ethoxyphenyl)-2,2-dichlorocyclopropane-1-carboxylic acid chloride and 4.36 g (0.02 mole) of 3-phenoxy-4-fluoro-benzyl alcohol were dissolved in 100 ml of anhydrous toluene, and 3 g of pyridine, dissolved in 50 ml of anhydrous toluene, were added dropwise at 20° to 25° C., while stirring. The reaction mixture was then stirred at 25° C. for a further 3 hours. It was poured into 150 ml of water, to which 10 ml of concentrated hydrochloric acid were added, and the organic phase was separated off and washed again with 100 ml of water. The toluene phase was then dried over sodium sulphate and the solvent was distilled off under a waterpump vacuum. Last residues of solvent were removed by brief incipient distillation at a bath temperature of 60° C./1 mm Hg. 8.1 g (85.3% of theory) of (±)-1-(4-ethoxy-phenyl)-2,2-dichlorocyclopropane-1-carboxylic acid 3-phenoxy-4-fluorobenzyl ester were obtained as a yellow oil. The structure was confirmed by the $^1$H-NMR spectrum.

$^1$H-NMR spectrum in CDCl$_3$/τ(ppm):
Cyclopropane H: 7.70 (quartet/2H)
Benzyl H: 4.97 (S/2H),
Ethyl H: 6.05 (quartet/2H) and 8.55 (t/3H).

The following compounds were obtained analogously:

Example 4

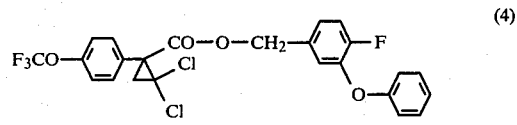

(4)

Example 5

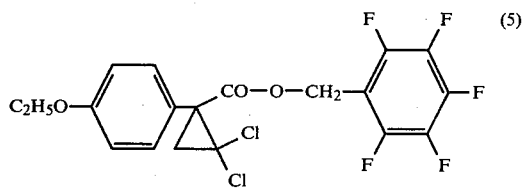

The insecticidal and acaricidal activity of compounds of this invention is illustrated by the following examples wherein the compounds according to the present invention are each identified by the number (given in brackets) from the corresponding preparative examples hereinabove:

Example 6

Myzus test

Solvent: 3 parts by weight of acetone
Emulsifier: 1 part by weight of alkylaryl polyglycol ether To produce a suitable preparation of active compound, 1 part by weight of the active compound was mixed with the stated amount of solvent containing the stated amount of emulsifier and the concentrate was diluted with water to the desired concentration.

Cabbage plants (*Brassica oleracea*) which had been heavily infested with peach aphids (*Myzus persicae*) were treated by being dipped into the preparation of active compound of the desired concentration.

After the specified periods of time, the degree of destruction was determined as a percentage; 100% meant that all of the aphids were killed whereas 0% meant that none of the aphids were killed.

In this test, for example, the following compounds showed a superior activity compared to the prior art: compounds (1), (2) and (3).

Example 7

Tetranychus test (resistant)

Solvent: 3 parts by weight of acetone
Emulsifier: 1 part by weight of alkylaryl polyglycol ether To produce a suitable preparation of active compound, 1 part by weight of active compound was mixed with the stated amount of solvent and the stated amount of emulsifier, and the concentrate was diluted with water to the desired concentration.

Bean plants (*Phaseolus vulgaris*) which were heavily infested with the common spider mite or two-spotted spider mite (*Tetranychus urticae*) in all stages of development were treated by being dipped into the preparation of the active compound of the desired concentration.

After the specified periods of time, the destruction in % was determined. 100% meant that all the spider mites had been killed, 0% meant that none of the spider mites had been killed.

In this test, for example, the following compounds showed a superior activity compared to the prior art: compounds (1), (2) and (3).

Example 8

Test insect: *Agrotis segetum* larvae (in the soil)
Solvent: 3 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

The preparation of active compound was intimately mixed with the soil. The concentration of the active compound in the preparation was practically immaterial, the only decisive factor being the amount by weight of active compound per unit volume of soil, which is quoted hereinafter in ppm (=mg/l). The treated soil was filled into pots and the pots were left to stand at room temperature.

After 24 hours the test insects were introduced into the treated soil and after a further 2 to 7 days the degree of effectiveness of the active compound was determined in % by counting the dead and the live test insects. The degree of effectiveness was 100% if all of the test insects had been killed and was 0% if exactly as many test insects were still alive as in the case of the untreated control.

In this test, for example, the following compound showed a superior action compared to the prior art: compound (1).

Example 9

Test insect: *Phorbia antiqua* maggots (in the soil)
Solvent: 3 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

The preparation of active compound was intimately mixed with the soil. The concentration of the active compound in the preparation was practically immaterial, the only decisive factor being the amount by weight of active compound per unit volume of soil, which is quoted hereinafter in ppm (=mg/l). The treated soil was filled into pots and the pots were left to stand at room temperature.

After 24 hours the test insects were introduced into the treated soil and after a further 2 to 7 days the degree of effectiveness of the active compound was determined in % by counting the dead and the live test insects. The degree of effectiveness was 100% if all of the test insects had been killed and was 0% if exactly as many test insects were still alive as in the case of the untreated control.

In this test, for example, the following compound showed a superior action compared to the prior art: compound (2).

Example 10

LD$_{100}$ test

Test insects: *Sitophilus granarius*
Number of test insects: 25

Solvent: Acetone

The active compound was taken up in the solvent at a rate of 2 g per liter. The solution so obtained was diluted with further solvent to the desired concentrations.

2.5 ml of the solution of the active compound were pipetted into a Petri dish. On the bottom of the Petri dish there was a filter paper with a diameter of about 9.5 cm. The Petri dish remained uncovered until the solvent had completely evaporated. The amount of active compound per square meter of filter paper varied with the concentration of the solution of active compound. The stated number of test insects was then placed in the Petri dish and the dish was covered with a glass lid.

The condition of the test insects was observed 3 days after the commencement of the experiments. The destruction, in %, was determined. 100% meant that all of the test insects had been killed; 0% meant that none of the test insects had been killed.

In this test, for example, the following compounds showed a superior action compared to the prior art: compounds (1) and (3).

Example 11

Test with *Boophilus microplus* resistant

Solvent:
35 parts by weight of ethylene glycol monomethyl ether
35 parts by weight of nonylphenol polyglycol ether To produce a suitable preparation of active compound, three parts by weight of active compound were mixed with seven parts by weight of the solvent mixture indicated above, and the concentrate thus obtained was diluted with water to the desired concentration.

10 Adult *Boophilus microplus* res, were immersed for 1 minute in the active compound preparation to be tested. After transfer to plastic beakers and storage in a climatically controlled chamber, the degree of destruction was determined.

In this test, for example, the following compound showed a superior action compared to the prior art: compound (1).

Example 12

Test with *Psoroptes cuniculi*

Solvent:
35 parts by weight of ethylene glycol monomethyl ether
35 parts by weight of nonylphenol polyglycol ether To produce a suitable preparation of active compound, three parts by weight of active compound were mixed with seven parts by weight of the solvent mixture indicated above, and the concentrate thus obtained was diluted with water to the desired concentration.

About 10-25 *Psoroptes cuniculi* were introduced into 1 ml of the active compound preparation to be tested, which had been pipetted into tablet nests of a deep-drawn pack. After 24 hours, the degree of destruction was determined.

In this test, for example, the following compound showed a superior action compared to the prior art: compound (1).

It will be appreciated that the instant specification and examples are set forth by way of illustration and not limitation, and that various modifications and changes may be made without departing from the spirit and scope of the present invention.

We claim:

1. A 1-aryl-cyclopropane-1-carboxylic acid ester of the formula

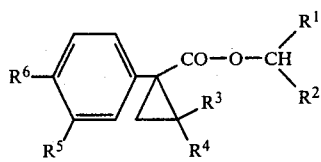

in which
$R^1$ represents a hydrogen atom, a cyano radical or an alkyl, alkenyl or alkinyl radical with in each case up to 7 carbon atoms, and
$R^2$ represents a phenyl radical which is substituted by halogen and/or optionally halogen-substituted phenoxy, with the proviso that the radical $R^2$ in total contains at least one fluorine substituent,
$R^3$ and $R^4$, which can be identical or different, represents a fluorine, chlorine or bromine atom or a methyl radical,
$R^5$ represents a hydrogen or halogen atom or a methyl or methoxy radical, and
$R^6$ represents a hydrogen or halogen atom, a cyano nitro or amino radical or an optionally halogen-substituted radical selected from $C_1$ to $C_4$ alkyl, $C_1$ to $C_4$ alkoxy and $C_1$ to $C_4$ alkylthio,
or wherein
the two radicals $R^5$ and $R^6$ together represent an optionally halogen-substituted $C_1$ or $C_2$ alkylenedioxy radical.

2. A compound according to claim 1 in which
$R^1$ represents a hydrogen atom or a cyano radical,
$R^2$ represents a 4-fluoro-3-phenoxy-phenyl, 3-(4-fluoro-phenoxy)-phenyl, 4-fluoro-3-(4-fluorophenoxy)-phenyl or pentafluorophenyl radical,
$R^3$ and $R^4$ represent chlorine atoms,
$R^5$ represents a hydrogen atom and
$R^6$ represents a fluorine, chlorine or bromine atom or a methoxy, ethoxy, trifluoromethoxy, 2-chloro-1,1,2-trifluoroethoxy or 1,1,2,2-tetrafluoroethoxy radical, or
$R^5$ and $R^6$ together represent a methylenedioxy or difluoromethylenedioxy radical.

3. A compound according to claim 1, wherein such compound is 1-(4-trifluoromethoxy-phenyl)-2,2-dichloro-cyclopropane-1-carboxylic acid 3-phenoxy-4-fluoro-α-cyano-benzyl ester of the formula

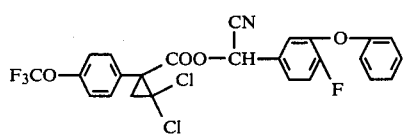

4. A compound according to claim 1, wherein each compound is 1-(4-ethoxyphenyl)-2,2-dichlorocyclopropane-1-carboxylic acid 3-phenoxy-4-fluoro-α-cyano-benzyl ester of the formula

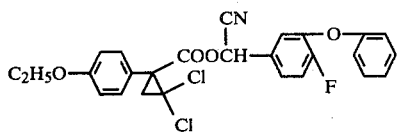

5. A compound according to claim 1, wherein such compound is 1-(4-ethoxyphenyl)-2,2-dichlorocyclopropane-1-carboxylic acid 3-phenoxy-4-fluoro-benzyl ester of the formula

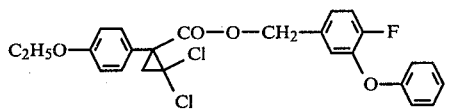

6. A compound according to claim 1, wherein such compound is 1-(4-trifluoromethoxy-phenyl)-2,2-dichlorocyclopropane-1-carboxylic acid 3-phenoxy-4-fluoro-benzyl ester of the formula

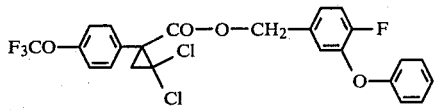

7. A compound according to claim 1, wherein such compound is 1-(4-ethoxy-phenyl)-2,2-dichlorocyclopropane-1-carboxylic acid pentafluorobenzyl ester of the formula

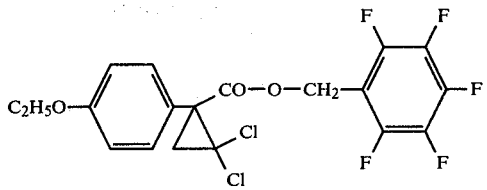

8. A pesticidal composition comprising a pesticidally effective amount of a compound according to claim 1 in admixture with a diluent.

9. A method of combating pests comprising applying to the pests, or to a habitat thereof, a pesticidally effective amount of a compound according to claim 1.

10. The method according to claim 9 wherein such compound is 1-(4-trifluoromethoxy-phenyl)-2,2-dichloro-cyclopropane-1-carboxylic acid 3-phenoxy-4-fluoro-α-cyano-benzyl ester, 1-(4-ethoxyphenyl)-2,2-dichlorocyclopropane-1-carboxylic acid 3-phenoxy-4-fluoro-α-cyano-benzyl ester, 1-(4-ethoxyphenyl)-2,2-dichlorocyploroapne-1-carboxylic acid 3-phenoxy-4-fluoro-benzyl ester, 1-(4-trifluoromethoxy-phenyl)-2,2-dichlorocyclopropane-1-carboxylic acid 3-phenoxy-4-fluoro-benzyl ester or 1-(4-ethoxy-phenyl)-2,2-dichlorocyclopropane-1-carboxylic acid pentafluorobenzyl ester.

* * * * *

UNITED STATES PATENT AND TRADEMARK OFFICE
CERTIFICATE OF CORRECTION

PATENT NO. : 4,360690
DATED : November 23, 1982
INVENTOR(S) : Rainer Fuchs et al It is certified that error appears in the above—identified patent and that said Letters Patent is hereby corrected as shown below:

Col. 2, line 60  Delete "phenoxy-phenoxy" and insert --phenoxy-phenyl--
Col. 6, line 11  Delete "Porcello" and insert --Porcellio--
Col. 8, line 1   Delete "A" and insert --"As--
Col. 14, line 65 Delete "each" and insert --such--
Col. 16, line 28 Delete "dichlorocyclicproapne" and insert --dichlorocyclopropane--

Signed and Sealed this

First Day of February 1983

[SEAL]

Attest:

GERALD J. MOSSINGHOFF

Attesting Officer    Commissioner of Patents and Trademarks